US007758589B2

(12) United States Patent
Ortiz et al.

(10) Patent No.: US 7,758,589 B2
(45) Date of Patent: Jul. 20, 2010

(54) SURGICAL INSTRUMENT FOR EXTRACTING AN ANASTOMOTIC RING DEVICE (75) Inventors: Mark S. Ortiz, Milford, OH (US); Lynetta Freeman, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 582 days.

(21) Appl. No.: 11/120,826

(22) Filed: May 3, 2005

(65) Prior Publication Data

US 2006/0253134 A1 Nov. 9, 2006

(51) Int. Cl.
*A61B 17/10* (2006.01)
(52) U.S. Cl. ...................... 606/108; 606/153
(58) Field of Classification Search ............. 606/108, 606/153, 138, 113, 127, 206; 600/104, 214–217
See application file for complete search history.

(56) References Cited

U.S. PATENT DOCUMENTS

| 5,843,121 | A  | * | 12/1998 | Yoon ............................ 606/206 |
| 6,187,016 | B1 | * | 2/2001  | Hedges et al. ............... 606/108 |
| 6,241,738 | B1 | * | 6/2001  | Dereume ..................... 606/108 |
| 6,352,503 | B1 | * | 3/2002  | Matsui et al. ................ 600/104 |
| 6,605,104 | B2 | * | 8/2003  | Sato et al. .................... 606/206 |
| 6,679,893 | B1 | * | 1/2004  | Tran ............................. 606/127 |
| 7,029,435 | B2 | * | 4/2006  | Nakao ......................... 600/153 |

| 2002/0161377 | A1 |   | 10/2002 | Rabkin |
| 2003/0032967 | A1 |   | 2/2003  | Park et al. |
| 2003/0060876 | A1 |   | 3/2003  | Loshakove et al. |
| 2005/0080431 | A1 | * | 4/2005  | Levine et al. ................ 606/108 |
| 2007/0203503 | A1 | * | 8/2007  | Salahieh et al. ............. 606/108 |

FOREIGN PATENT DOCUMENTS

EP 0829242 3/1998

OTHER PUBLICATIONS

European Search Report, dated Sep. 18, 2006, for EP Application No. 06252327.9.

* cited by examiner

*Primary Examiner*—Todd E Manahan
*Assistant Examiner*—Katherine M Dowe (57) ABSTRACT

A surgical instrument comprises a handle and an elongate shaft, and is operable to remove an anastomotic ring device from a patient. The elongate shaft houses a plurality of ring engaging fingers. Each of the fingers comprises sheath housing a wire having a hook at its distal end. Each hook may be advanced beyond the distal end of a respective sheath to engage petals on an anastomotic ring device. Subsequent proximal retraction of the hooks secures the anastomotic ring device to the ring engaging fingers. With the anastomotic ring device secured to the ring engaging fingers, the fingers may be drawn together to collapse the anastomotic ring device from an actuated, hollow rivet-shaped configuration to an unactuated, cylindrically-shaped configuration. The surgical instrument may then contain the collapsed anastomotic ring device, thereby facilitating removal of the anastomotic ring device from the patient.

17 Claims, 10 Drawing Sheets

SURGICAL INSTRUMENT FOR EXTRACTING AN ANASTOMOTIC RING DEVICE

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

However, it is possible that an application device may misfire when positioning the anastomotic ring device. This may leave the anastomotic ring device incorrectly deployed in the patient's body. Alternatively, other reasons may exist for desiring the removal of an anastomotic ring device. With anastomotic rings that are generally designed to be biased to the actuated position, it may necessary or otherwise desirable to at least partially compress the ring to the unactuated position to facilitate removal of the anastomotic ring device. Other reasons may exist for compressing an anastomotic ring device to an unactuated position for removal.

Accordingly, it may be desirable to have an extractor device that is operable to remove an anastomotic ring device from a patient's body.

BRIEF SUMMARY OF THE INVENTION

Embodiments of the present invention provide a surgical instrument for extracting an anastomotic ring device. In one embodiment, a surgical instrument comprises a handle and an elongate shaft, and is operable to remove an anastomotic ring device from a patient. The elongate shaft houses a plurality of ring engaging fingers. Each of the fingers comprises sheath housing a wire having a hook at its distal end. Each hook may be advanced beyond the distal end of a respective sheath to engage petals on an anastomotic ring device. Subsequent proximal retraction of the hooks secures the anastomotic ring device to the ring engaging fingers. With the anastomotic ring device secured to the ring engaging fingers, the fingers may be drawn together to collapse the anastomotic ring device from an actuated, hollow rivet-shaped configuration to an unactuated, cylindrically-shaped configuration. The surgical instrument may then contain the collapsed anastomotic ring device, thereby facilitating removal of the anastomotic ring device from the patient.

In another embodiment, an instrument comprises a handle, a ring engagement mechanism that is operable to engage a deployed anastomotic ring, and a ring collapsing mechanism that is operable to collapse the ring from a deployed position to a compressed position in which the ring may be removed from the patient.

In another embodiment, an extractor device comprises a handle attached to an elongated sleeve that houses a ring engagement mechanism. The ring engagement mechanism comprises a plurality of ring-engaging members that are configured to grasp the outer circumference of the proximal end or face of a deployed anastomotic ring. The sleeve is operable to slide over the ring-engaging members after they have engaged the proximal end or face of the anastomotic ring and collapse the ring to its compressed state.

In yet another embodiment, an extractor device comprises a handle attached to an elongated sleeve that houses a plurality of ring-engaging members, each having a proximal end and a distal end. The distal ends of the ring-engaging members are configured to flare out from the longitudinal axis of the elongated sleeve in order to engage the outer circumference of the proximal end or face of the anastomotic ring. The sleeve is operable to slide over the distal ends of the ring-engaging members after they have engaged the proximal end of the anastomotic ring, thereby bringing them into parallel alignment with the elongated sleeve, thereby causing the proximal end of the anastomotic ring to collapse into the unactuated, cylindrically-shaped position. The sleeve may be advanced through the anastomotic opening and over the distal end of the anastomotic ring, thereby ensuring the collapse the distal end of the anastomotic ring into the unactuated, cylindrical-shaped position. The anastomotic ring may then be contained in the sleeve for removal from the patient.

In still another embodiment, an extractor device comprises a handle and an elongate shaft extending therefrom. The device further comprises a plurality of ring-engaging fingers housed within the elongate shaft. Each ring-engaging member comprises a hook sheath housing a ring-engaging member having a proximal end and a distal end. The distal end of each ring-engaging member terminates in a hook. The hooks are moveable from a first position, in which the hook is contained within the sheath, to a second position, in which the hook extends from the sheath. The distal ends of the hook sheaths are flared such that in their extended position, the hooks are positioned to engage the outer circumference of the proximal end or face of the anastomotic ring. The extractor device further comprises a sleeve configured to slide over the ring engaging fingers after the hooks have engaged the proximal end or face of the anastomotic ring. The sleeve is further configured to slide through the anastomotic opening and over the distal end of the anastomotic ring.

Another embodiment includes a method for extracting a deployed anastomotic ring. The method includes inserting an elongate shaft of a surgical instrument into a patient's body adjacent a deployed anastomotic ring; engaging the outer circumference of the proximal end or face of the anastomotic ring with a plurality of ring-engaging members; advancing a sleeve of the elongated shaft over the ring-engaging members to collapse the proximal end of the anastomotic ring from the actuated position to the unactuated position; advancing the sleeve through the anastomotic opening; collapsing the distal end of the anastomotic ring from the actuated position to the unactuated position; and removing the instrument with the compressed anastomotic ring.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF THE INVENTION

Figure 1:
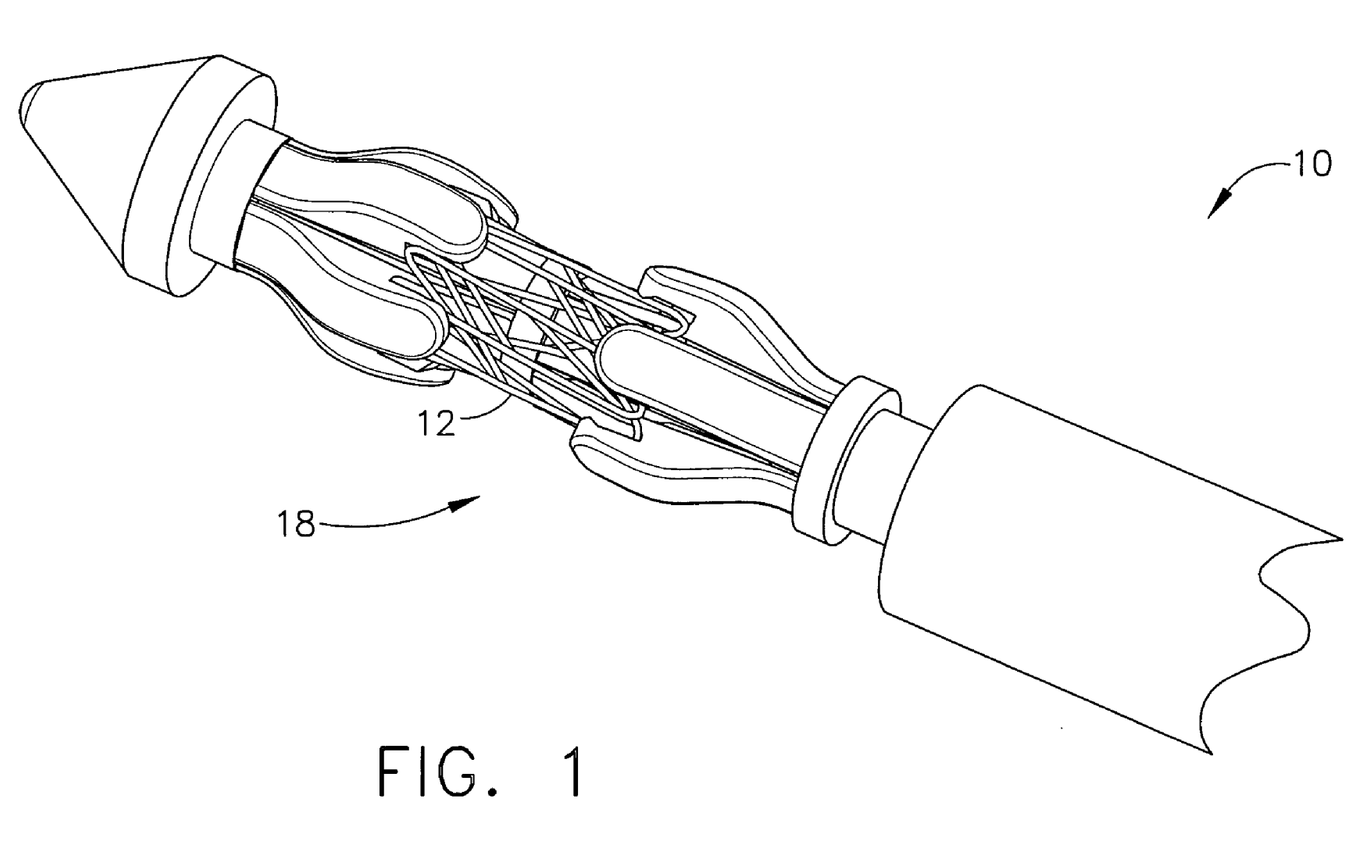
FIG. 1 is a partial perspective view of the distal portion of an anastomotic ring applier device holding an anastomotic ring in an unactuated position.
Figure 2:
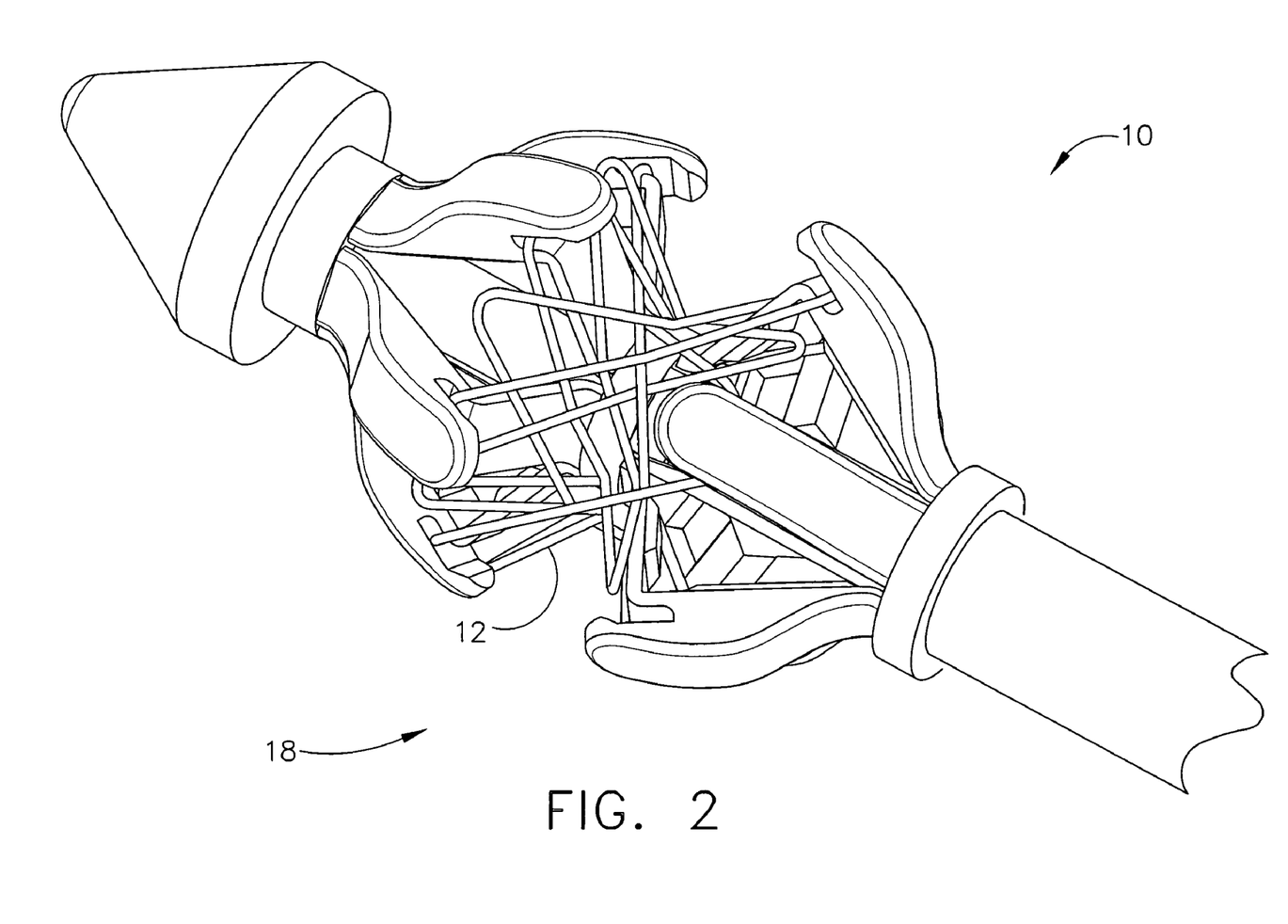
FIG. 2 is a partial perspective view of the distal portion of the device of FIG. 2 shown without a sheath holding an anastomotic ring in the actuated position.
Figure 3:
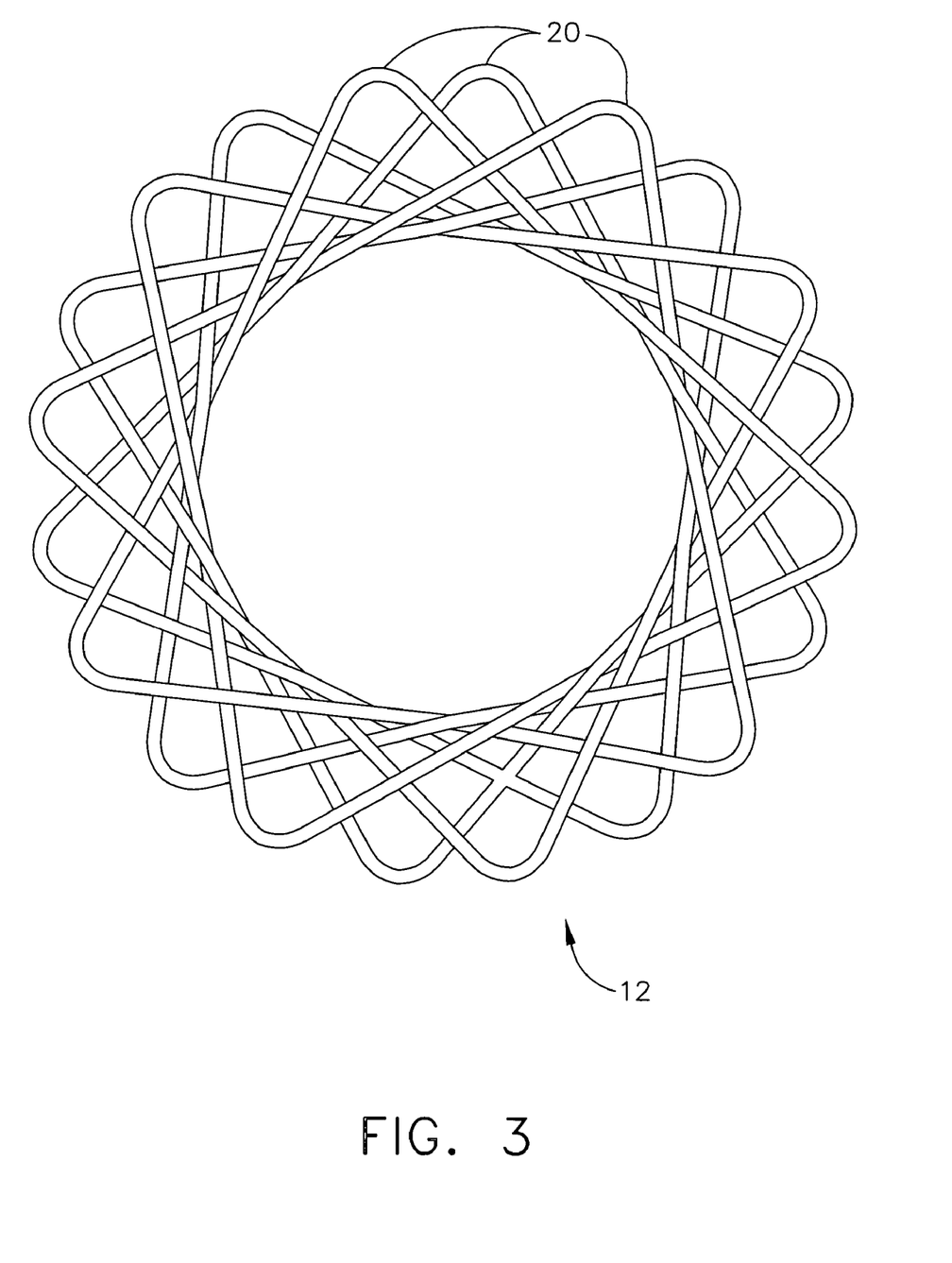
FIG. 3 is a frontal view of an actuated anastomotic ring.
Figure 4:
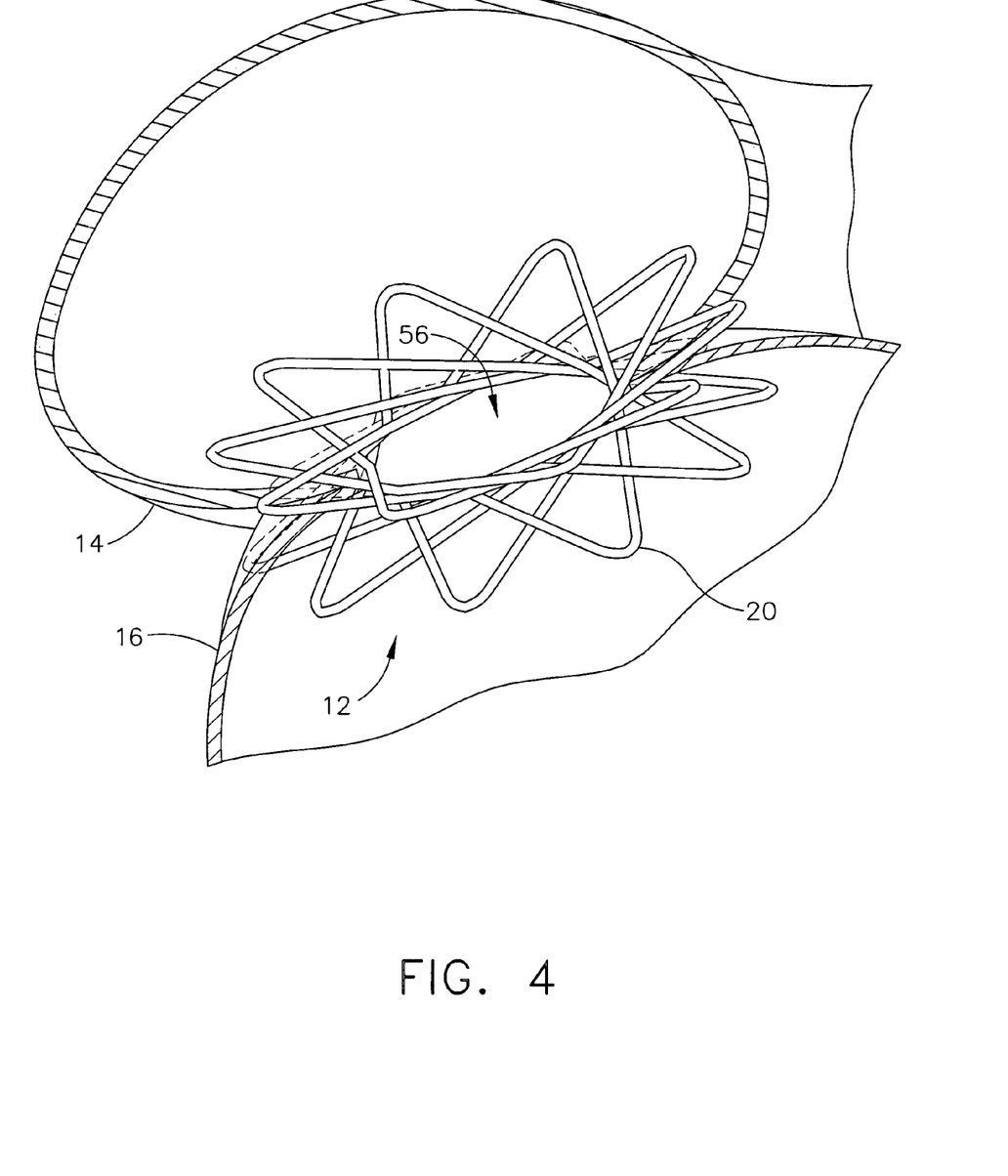
FIG. 4 is a perspective, partial cross-sectional view of an anastomotic ring device in a fully actuated position forming an anastomotic attachment between proximate gastrointestinal passage tissue walls.
Figure 5:
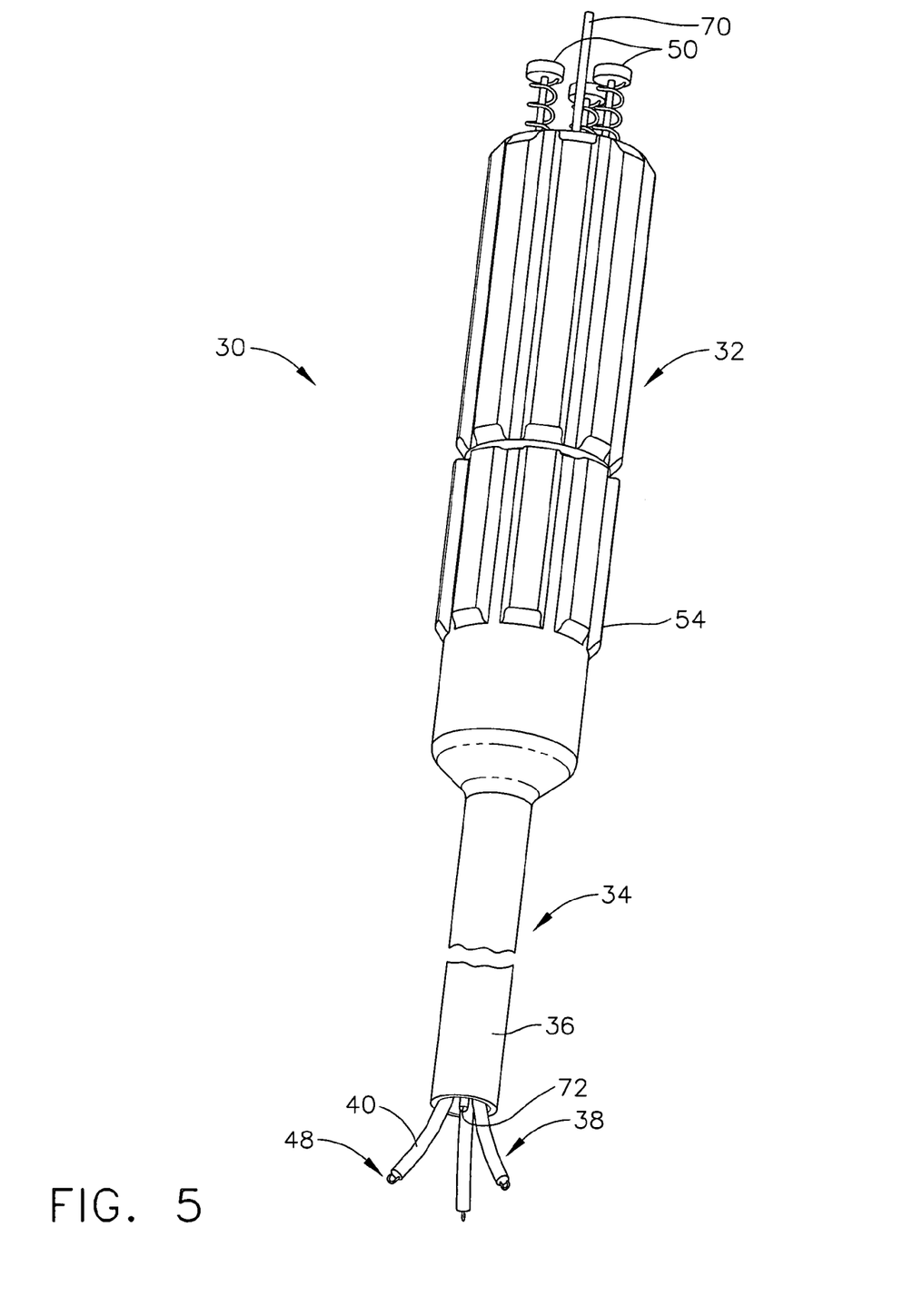
FIG. 5 is a perspective view of an embodiment of a surgical instrument for extracting an anastomotic ring device.
Figure 6:
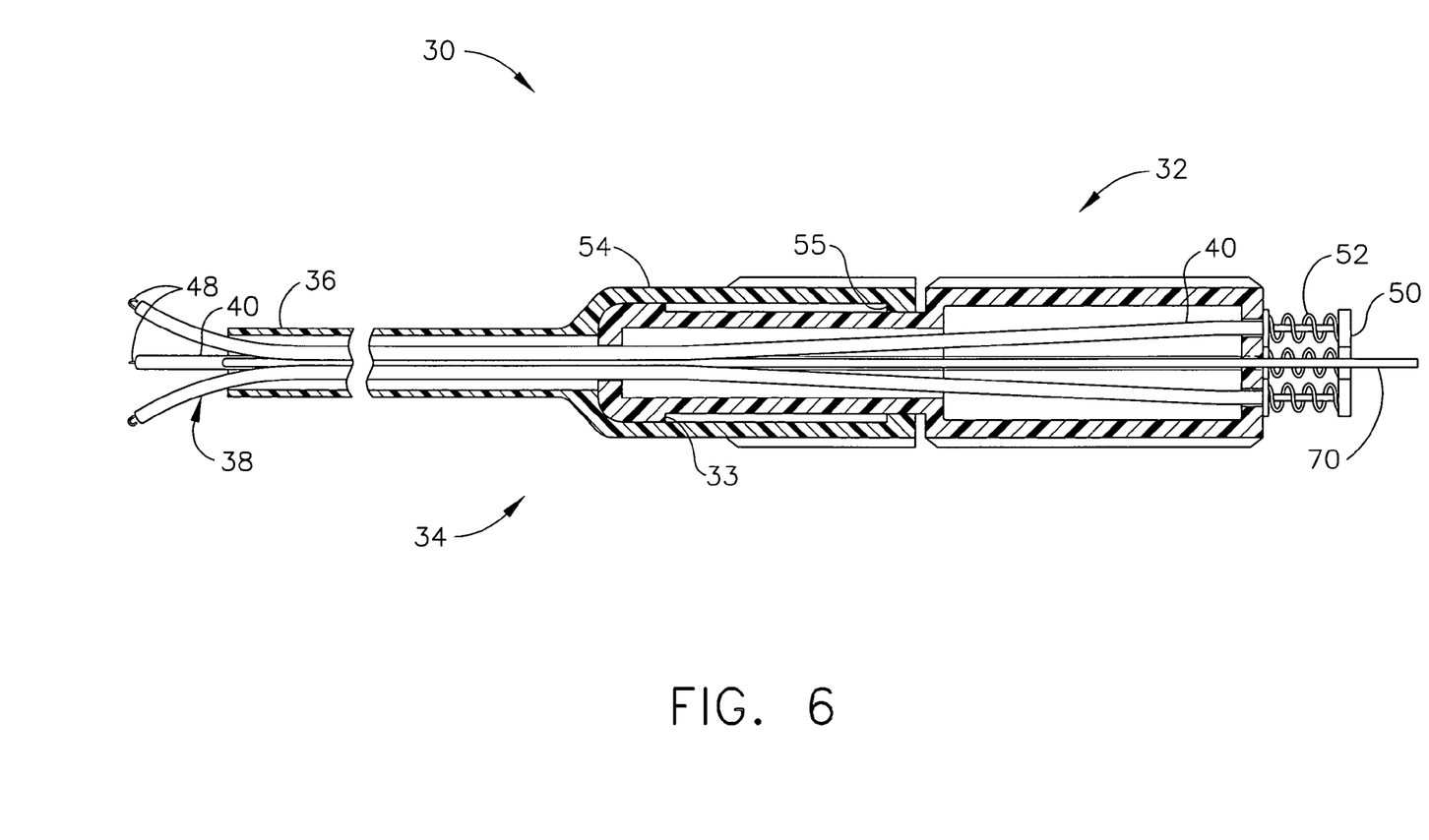
FIG. 6 is a cross-sectional view of the instrument of FIG. 5, taken along a longitudinal plane of the instrument.

Turning to the drawings, wherein like numerals denote like components throughout the several views, FIGS. 1 and 2 depict an applier 10 that is operable to deploy and actuate an anastomotic ring device 12 from a generally cylindrical shape (FIG. 1) to one having properties of a hollow rivet, or ring (FIG. 2), capable of forming an anastomotic attachment at an anastomosis target site, such as in a bariatric gastric bypass of a morbidly obese patient. It will be appreciated that applier 10 may be used in a variety of ways, including but not limited to laparoscopically or endoscopically. Applier 10 is shown in FIGS. 1 and 2 with an anastomotic ring 12 on a deployment mechanism 18. In FIG. 1, anastomotic ring 12 is shown in the compressed, cylindrically-shaped position. In FIG. 2, deployment mechanism 18 of applier 10 has moved anastomotic ring 12 to the actuated, hollow rivet-shaped position. FIG. 3 is a close-up view of anastomotic ring 12 in the actuated position. FIG. 4 shows anastomotic ring 12 in the actuated position, forming an anastomotic attachment between tissue walls 14, 16. As shown, in the fully actuated position, the circumference of anastomotic ring 12 comprises a number of petals 20. It will be appreciated that anastomotic ring 12 may help maintain an anastomotic opening 56 formed in adjacent tissue walls 14, 16.

Anastomotic ring 12 may comprise a shape memory effect (SME) material, such as nitinol by way of example only, that further assists in actuation to an engaging hollow rivet shape. Other suitable anastomotic ring 12 materials will be apparent to those of ordinary skill in the art. An exemplary anastomotic ring 12 is described in detail in U.S. Patent Application Publ. No. US 2003/0032967 to Park et al.

It will be appreciated that the terms "proximal" and "distal" are used herein with reference to a clinician gripping a handle of an instrument. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

FIGS. 5-8 show a merely exemplary embodiment of a ring extractor 30. Extractor 30 comprises a handle 32 and a hollow, elongate shaft 34. Shaft 34 is slidably attached to handle 32, such that sleeve 36 may slide longitudinally reltative to handle 32. The distal portion of shaft 34 comprises a sleeve 36, while the proximal portion of shaft 34 comprises a sleeve actuator 54. Sleeve actuator 54 is configured to communicate longitudinal motion to sleeve 36 with relative to handle 32. As shown, the distal end of handle 32 comprises an outer circumferential flange 33, while the proximal end of sleeve actuator 54 comprises an inner circumferential flange 55. Flanges 33, 55 are configured to prevent inadvertent longitudinal overextension of shaft 34 with relative to handle 32. Various alternative configurations for handle 32 and shaft 34 will be apparent to those of ordinary skill in the art.

Figure 7:
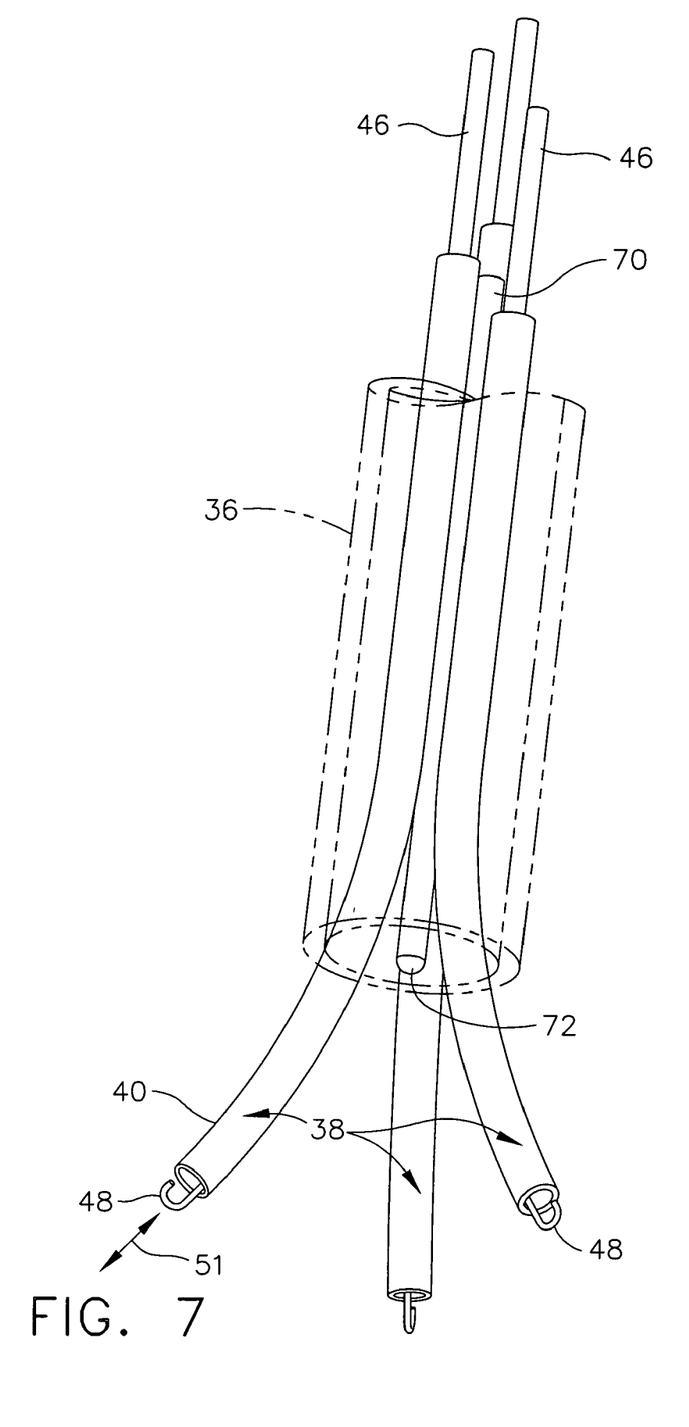
FIG. 7 is a partial perspective view of a ring compression mechanism of the instrument of FIG. 5.

In the present example, sleeve 36 houses a plurality of ring-engaging fingers 38. As best shown in FIG. 7, each finger 38 comprises a sheath 40 containing a respective wire 46. The distal end of each wire 46 terminates in a hook 48 configured to engage petals 20 of ring device 12. Each wire 46 and respective hook 48 thus forms a ring engaging member. Those of ordinary skill in the art will appreciate, however, that ring engaging members may comprise a variety of alternative components, features, and/or configurations. For instance, and without limitation, hooks 48 may be substituted with any substantially hook-shaped member, or any other structure configured to engage petals 20 of anastomotic ring device 12.

In one embodiment, the distal end of each wire 46 is simply bent to form a respective hook 48. In another embodiment, each wire 46 and hook 48 are formed separately, then each hook 48 is fixedly secured to the distal end of a respective wire 46. Of course, wires 46 may be configured to engage ring device 12 by any other suitable means. In the present example, extractor 30 comprises three ring-engaging fingers 38. Fingers 38 are configured to engage outer circumference of anastomotic ring 12 at separations of approximately 120°. In the present example, fingers 38 are configured such that they are urged to flare outward with respect to the longitudinal axis of extractor 30. In one embodiment, wires 46 or another portion of the ring engaging members are configured such that they are urged to flare outward with respect to the longitudinal axis of extractor 30. In another embodiment, sheaths 40 are configured such that they are urged to flare outward with respect to the longitudinal axis of extractor 30. It will be appreciated that any other number of fingers 38 may be used, that fingers 38 may have any other features, components, or configurations, and that fingers 38 may be positioned at any suitable spacing.

In the present example, wire 46 is moveable from a first, unactuated position, in which hook 48 is substantially contained within sheath 40, to a second, actuated position, in which a substantial portion of hook 48 extends beyond the distal end of sheath 40. To facilitate such movement, handle 32 comprises a plurality of hook actuator buttons 50, each of which is in communication with a respective wire 46. In this configuration, actuation of actuator buttons 50 causes wires 46, and hence hooks 48, to move from the first position to the second position. The directions of motion of hooks 46 is depicted by arrow 51 in FIG. 7.

Figure 8:
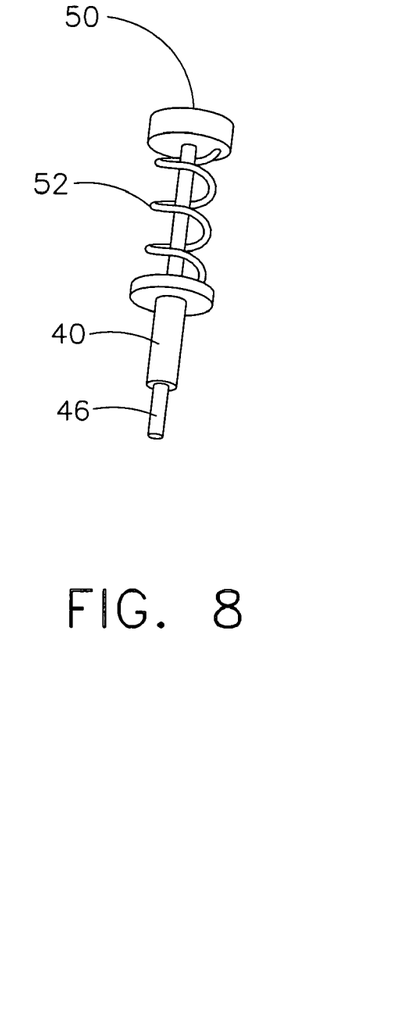
FIG. 8 is a partial perspective view of a hook actuator mechanism of the instrument of FIG. 5.

As pictured in FIG. 8, each hook actuator button 50 is in communication with a respective compression spring 52. Each compression spring 52 biases a respective hook actuator button 50, and thus biases a respective wire 46 and hook 48, to the first, unactuated position. In order to move hooks 48 to the second, actuated position to engage petals 20 of ring device 12, the surgeon actuates actuator buttons 50. When the surgeon releases actuator buttons 50, bias of springs 52 cause hooks 48 to return to their respective first, unactuated positions within sheaths 40. Using springs 52 to bias wires 46 and hooks 48 to the first, unactuated position may serve at least two purposes: (i) preventing inadvertent engagement of ring device 12 when positioning extractor 30; and (ii) locking the engagement of hooks 48 to petals 20 of ring device 12. Of course, such biasing may serve other purposes, or may be eliminated altogether. Indeed, those of ordinary skill in the art will immediately recognize that a variety of alternative configurations and mechanisms exist for effecting engagement of hooks 48 or other members with a ring device 12.

To remove a deployed ring device 12, extractor 30 may be inserted into the patient adjacent gastrointestinal passage tissue walls 14, 16. In operation, an endoscope may be used to view an anastomotic opening 56 where ring device 12 is deployed. The endoscope may assist the surgeon in positioning extractor device 30. Alternatively, and as shown in the present example, extractor 30 may comprise an imaging fiber 70 having an imaging element 72 at its distal end positioned along the longitudinal axis of extractor 30. Other ways for effecting visualization of the anastomosis site during use of extractor 30 will be apparent to those of ordinary skill in the art.

As illustrated in FIG. 4, ring device 12 of the present example assumes a hollow rivet shape when in the actuated position, comprising a proximal face or end and a distal face or end. The proximal face or end of ring device 12 will normally be encountered first by extractor 30 upon its insertion into the patient. It will be appreciated that extractor 30 is operable to engage petals 20 on the proximal face or end of the ring device 12, then to urge ring 12 device to the unactuated, cylindrical position for removal from the anastomosis site.

Figure 9:
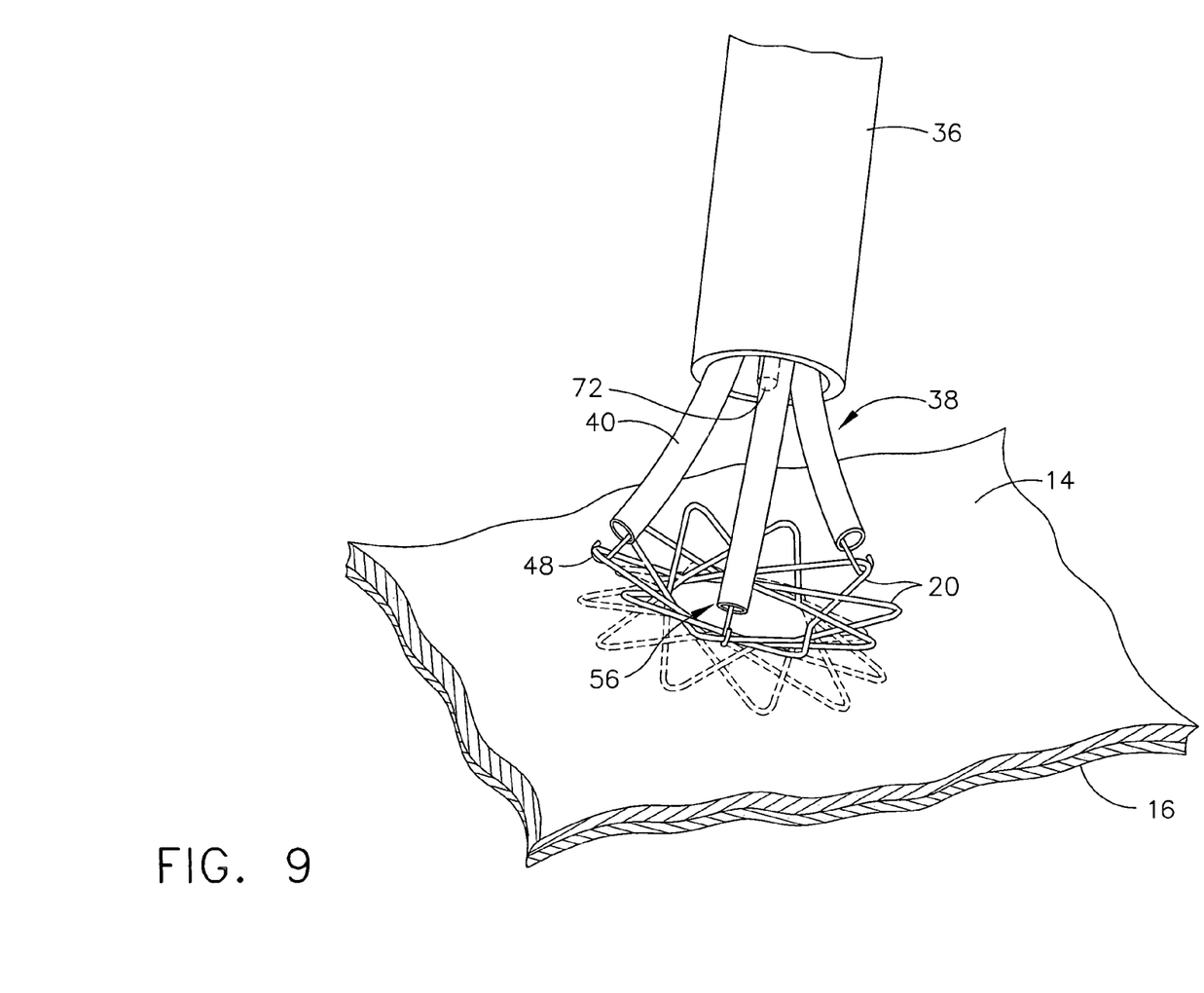
FIG. 9 is a partial side view of the instrument of FIG. 5, shown engaging the anastomotic ring device of FIG. 4.
Figure 10:
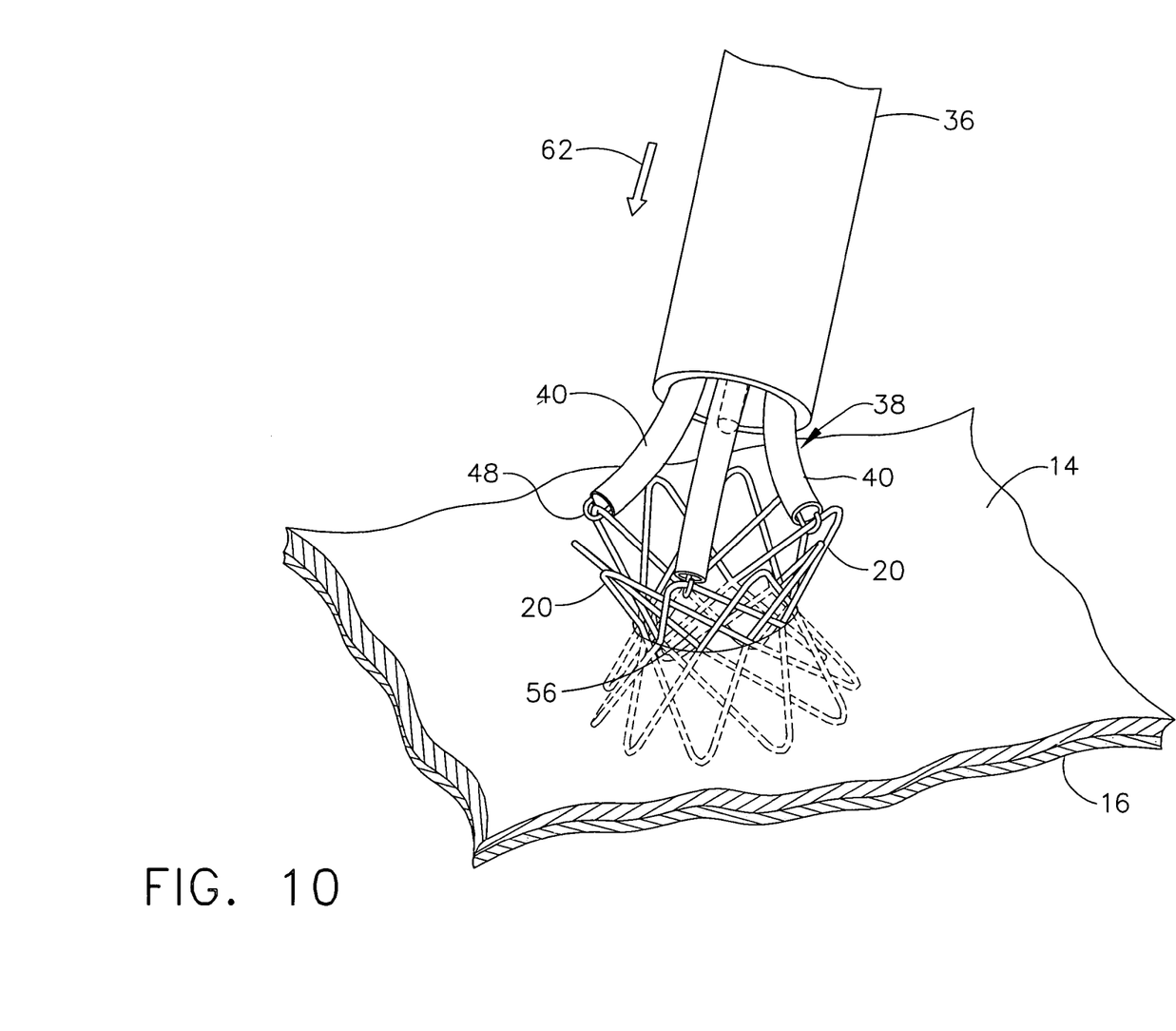
FIG. 10 is a partial side view of the instrument of FIG. 9, shown with the sleeve of the instrument advancing distally to compress the anastomotic ring device.
Figure 11:
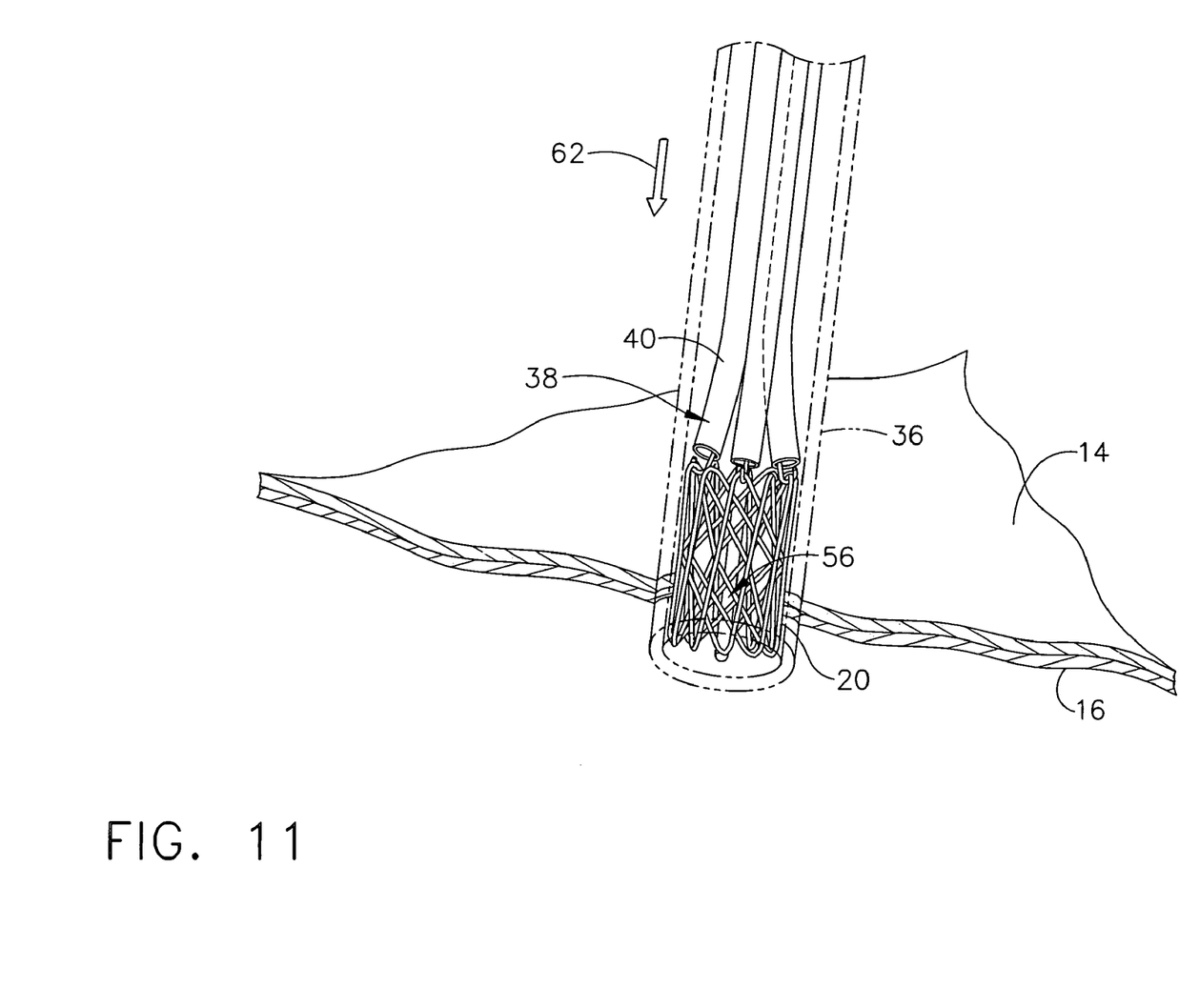
FIG. 11 is a partial side view of the instrument of FIG. 9, shown with the sleeve of the instrument advanced distally to contain the ring compression mechanism and the anastomotic ring device.

In a merely exemplary use, as shown in FIGS. 9-11, once extractor 30 is positioned at the anastomosis site, the surgeon engages actuator buttons 50 to move wires 46 from the first, unactuated position to the second, actuated position, thereby causing hooks 48 to extend from the distal ends of respective hook sheaths 40. When hooks 48 are in the extended or actuated position, the surgeon uses hooks 48 to grasp petals 20 on the proximal face of ring device 12, as shown in FIG. 9. Once hooks 48 have grasped petals 20, the surgeon releases actuator buttons 50, whereupon compression springs 52 urge hooks 48 to return to the first, unactuated position within each respective sheath 40, thus securing the engagement of ring 12 by hooks 48.

In order to fully collapse ring device 12, the surgeon engages sleeve actuator 54 to move sleeve 36 distally relative to handle 32, as depicted by arrow 62 in FIG. 10. As sleeve 36 is advanced distally over fingers 38, sleeve 36 draws distal ends 44 of sheaths 40 from the flared position depicted in FIGS. 5-9 toward longitudinal alignment with shaft 34. During this stage, because hooks 48 are securably grasping petals 20 of ring device 12, the movement of fingers 38 into longitudinal alignment with shaft 34 will collapse at least a portion of ring device 12 into a generally cylindrical shape. In the present example, due to the nature of the woven construction of ring device 12, the collapse of the proximal end or face of the ring device 12 will cause substantially corresponding collapse of the distal end or face of the ring device 12. Alternatively, the construction of a ring device may not provide such substantially corresponding collapse. It will be appreciated that extractor 30 may be useful with either type of anastomotic ring device, as well as other ring devices which will be apparent to those of ordinary skill in the art.

As shown in FIG. 11, the surgeon may further engage sleeve actuator 54 in order to continue to advance sleeve 36 distally over the distal ends of the fingers 38 and the ring device 12, through anastomotic opening 56. As sleeve 36 advances distally through anastomotic opening 56, distal end 60 of ring device 12 may be forced to further collapse into longitudinal alignment with shaft 34 until it is contained within sleeve 36. At that point, ring device 12 is in a substantially unactuated position, and is contained within sleeve 36. Ring device 12 may then be withdrawn from anastomotic opening 56 with extractor 30. Of course, the foregoing steps of operation are merely exemplary, and those of ordinary skill in the art will appreciate that extractor 30 may be used in a variety of different ways. In addition, it will be appreciated that any alternative to sleeve 36 for drawing fingers 38 toward the longitudinal axis of extractor 30 may be used.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A method of extracting an anastomotic ring device from an expanded position to a collapsed position using an instrument comprising:

a handle;

a hollow elongate sleeve having a proximal end and a distal end defining a longitudinal axis, wherein the elongate sleeve is slidably attached to the handle; and a plurality of ring-engaging members each having a proximal end integrally attached to the handle and a distal end, wherein a first portion of each ring engaging member is housed within the hollow of the elongate sleeve, wherein the distal ends of the ring-engaging members extend outwardly in a flared configuration from the distal end of the sleeve, wherein further each of the flared distal ends of the ring-engaging members are normally biased outwardly to engage an outer circumference the anastomotic ring device and each of the plurality of ring-engaging members are further configured to be individually movable in the longitudinal direction to individually engage with the anastomotic ring device without moving the other ring engaging members, wherein each of the ring engaging members comprises a wire, wherein each of the wires has a proximal end terminating at the handle, wherein each of the wires extends distally from the handle to a length longer than the sleeve, wherein each of the wires has a hook-shaped distal end, wherein the distal end of each wire curves proximally back toward the handle to form a hook shape before terminating;

wherein the sleeve is operable to slidably advance distally over the distal ends of the ring-engaging members after the ring-engaging members engage the anastomotic ring device, thereby drawing the normally outwardly biased distal ends of the ring-engaging members into longitudinal alignment with the sleeve to collapse the anastomotic ring device and to draw the distal ends and the collapsed anastomotic ring device into the hollow of the sleeve, the method comprising:

(a) positioning the plurality of ring-engaging members adjacent a deployed anastomotic ring device in a patient;
(b) individually engaging portions of the outer circumference of the anastomotic ring device with the plurality of ring-engaging members;
(c) advancing the hollow sleeve over the ring-engaging members to collapse at least a portion of the anastomotic ring device from the expanded position to the collapsed position;
(d) further advancing the hollow sleeve to bring the ring-engaging members and the anastomotic ring device within the hollow of the sleeve; and
(e) removing the ring-engaging members, hollow sleeve, and anastomotic ring device from the patient.

2. A for method of extracting an anastomotic ring device from an expanded state to a collapsed state using a surgical instrument comprising:

a handle;

an elongate shaft slidably attached to the handle, wherein the shaft comprises a hollow sleeve having a proximal end and a distal end defining a longitudinal axis therebetween;

a plurality of hook sheaths, each hook sheath having a proximal end integrally attached to the handle with a distal end extending from the hollow of the sleeve and a center portion housed within the sleeve, wherein the distal ends of the hook sheaths extending from the hollow of the sleeve are normally flared outwardly away from the longitudinal axis, with the center portion of the sheaths normally urged against an inner surface of the hollow sleeve; and a plurality of ring-engaging members integrally attached to the handle at a proximal end, each ring-engaging member integrally terminating in a distal hook for engaging the outer circumference of the anastomotic ring device, wherein each distal hook has a hook shape, such that a first portion of each distal hook extends distally then curves to extend proximally in a second portion before terminating, wherein each of the ring-engaging members is housed within a respective one of the hook sheaths, wherein each ring-engaging member is independently moveable longitudinally, without moving the other ring-engaging members, from a first position in which a substantial portion of the respective hook is contained within the respective hook sheath, to a second position in which a substantial portion of the respective hook protrudes from the respective hook sheath, and the plurality of ring-engaging members are deflected outwardly from the longitudinal axis by the normal bias of the plurality of hook sheaths;

wherein the sleeve is operable to distally advance toward the distal ends of the hooks, wherein the distal advancement of the sleeve moves the normally outwardly biased hook sheaths and hooks inwardly toward the longitudinal axis and into substantial longitudinal alignment with the inner surface of the sleeve, wherein further the sleeve is operable to distally advance over the over the entirety of each of the plurality of hooks and over the anastomotic ring device and thereby capture the anastomotic ring device in the hollow of the sleeve for removal, the method comprising:

(a) positioning the plurality of ring-engaging members adjacent a deployed anastomotic ring device in a patient;
(b) individually engaging portions of the outer circumference of the anastomotic ring device with the plurality of ring-engaging members;
(c) advancing the hollow sleeve over the ring-engaging members to collapse at least a portion of the anastomotic ring device from the expanded state to the collapsed state;
(d) further advancing the hollow sleeve to bring the ring-engaging members and the anastomotic ring device within the hollow of the sleeve; and
(e) removing the ring-engaging members, hollow sleeve, and anastomotic ring device from the patient.

3. A method of extracting an anastomotic ring device using an instrument comprising:

a handle;

an elongate shaft having a longitudinal axis and a proximal end and a distal end, wherein the elongate shaft extends distally from the handle and further comprises a hollow tube longitudinally movable relative to the handle;

a plurality of ring-engaging members integrally attached to the handle and having a portion of each of the plurality of ring-engaging members extending distally from the hollow of the tube, each ring-engaging member having a distal hook end configured to engage the outer circumference of the anastomotic ring device, wherein the distal hook ends are normally flared outwardly from the longitudinal axis of the elongate shaft and each of the plurality of ring-engaging members is configured to be moved individually in a longitudinal direction without moving the other ring engaging members;

a plurality of hook sheaths associated with the ring-engaging members, wherein each hook sheath surrounds a substantial portion of a respective ring-engaging member, wherein each hook sheath has a proximal end attached to the handle, wherein a distal end of each of the plurality of hook sheaths is configured to be adjacent to a respective distal hook end of the plurality of ring-engaging members when the plurality of ring-engaging members are in a proximal most position, wherein each of the ring engaging members is independently and resiliently biased to the proximal most position such that each of the distal hook ends is independently and resiliently biased to a proximal most position, wherein the distal hook end of each ring engaging member is substantially positioned within its associated hook sheath when the ring engaging member is in the proximal most position, wherein each distal hook end is in an unactuated position when the distal hook end of each ring engaging member is substantially positioned within its associated hook sheath; and wherein when one or more of the plurality of ring-engaging members moves to an actuated position, the respective distal hook end moves away from the adjacent respective hook sheath for reception of a portion of the anastomotic ring device therein, and when the respective distal hook end moves back to the unactuated position, the respective distal hook moves adjacent to the adjacent respective hook sheath to lock the portion of the anastomotic ring device to the surgical instrument and when the distal hook ends are attached to the anastomotic ring device, the surgical instrument is further configured to collapse the anastomotic ring device and to move the distal hook ends and the collapsed anastomotic ring into the hollow of the tube, the method comprising:

(a) positioning the plurality of ring-engaging members adjacent a deployed anastomotic ring device in a patient;

(b) individually engaging portions of the outer circumference of the anastomotic ring device with the plurality of ring-engaging members;

(c) advancing the hollow tube over the ring-engaging members to collapse at least a portion of the anastomotic ring device from an expanded state to a collapsed state;

(d) further advancing the hollow tube to bring the ring-engaging members and the anastomotic ring device within the hollow of the tube; and (e) removing the ring-engaging members, hollow tube, and anastomotic ring device from the patient.

4. A method of extracting a deployed anastomotic ring device from an anastomotic opening, the anastomotic ring device having a dual headed hollow rivet shape when deployed and a hollow tubular shape when undeployed, the method comprising:

(a) inserting an elongate shaft of a surgical instrument adjacent a deployed anastomotic ring device in a patient, wherein the anastomotic ring device has an outer circumference and the surgical instrument has a distal end for insertion into the patient and a proximal end outside of the patient and a longitudinal axis extending therebetween;

(b) individually engaging portions of the outer circumference of the anastomotic ring device with a plurality of individually movable ring-engaging members integral to the elongate shaft, wherein each of the ring-engaging members is configured to move in a longitudinal direction independently without moving the other ring engaging members;

(c) advancing a hollow sleeve of the elongate shaft entirely over the ring-engaging members to collapse at least a portion of the anastomotic ring from an actuated, hollow rivet-shaped position to an unactuated, cylindrical-shaped position;

(d) further advancing the sleeve through the anastomotic opening to bring the ring engaging members entirely within the sleeve along with and the remainder of the anastomotic ring; and (e) removing the shaft from the patient.

5. The method of claim 4, wherein the act of engaging comprises engaging one or more actuator buttons to move the ring-engaging members from a first position, in which a distal portion of each of the ring-engaging members is contained in a respective sheath, to a second position, in which the distal portion of each of the ring-engaging members extends from the respective sheath.

6. A method of extracting a normally expanded anastomotic ring device using a surgical instrument, the anastomotic ring device having a hollow tubular shape when compressed and a hollow, expanded dual headed rivet shape when expanded for clamping tissue between the expanded dual heads, the surgical instrument comprising:

a handle;

an elongate shaft defining a longitudinal axis and slidably engaged with the handle, the elongate shaft comprising a hollow sleeve movable proximally and distally along the longitudinal axis relative to the handle, wherein the sleeve has a distal edge; and a plurality of elongate fingers extending longitudinally through the hollow of the sleeve and extending distally therefrom, wherein a distal end of each of the fingers is configured to engage with a portion of an expanded head of the anastomotic ring device and the plurality of elongate fingers are normally biased to flare outwardly away from the longitudinal axis and into contact with an inner surface of the hollow of the sleeve;

wherein each of the plurality of elongate fingers integrally attached to the handle is individually movable in the longitudinal direction without moving the other fingers, to individually engage the distal end of the finger with a portion of the expanded head of the anastomotic ring device, and the distal end of each of the flared plurality of elongate fingers is further configured to move inwardly toward the longitudinal axis in response to longitudinal movement of the sleeve to inwardly collapse the engaged expanded anastomotic ring device to the hollow tubular shape and to fully receive the plurality of elongate fingers and the attached anastomotic ring device within the hollow of the sleeve;

wherein the sleeve and the elongate fingers are configured such that the sleeve is movable distally to a position where the distal ends of the elongate fingers are proximal to the distal edge of the sleeve, such that the sleeve is configured to longitudinally capture the entirety of the attached anastomotic ring along a length of the sleeve between the distal ends of the elongate fingers and the distal edge of the sleeve, the method comprising:

(a) positioning the distal ends of the elongate fingers adjacent a deployed anastomotic ring device in a patient;

(b) individually engaging portions of the outer circumference of the anastomotic ring device with the distal ends of the elongate fingers;

(c) advancing the hollow sleeve over the elongate fingers to collapse at least a portion of the anastomotic ring device from the expanded dual headed rivet shape to the tubular shape;

(d) further advancing the hollow sleeve to bring the distal ends of the elongate fingers and the anastomotic ring device within the hollow of the sleeve; and (e) removing the elongate fingers, hollow sleeve, and anastomotic ring device from the patient.

7. The method of claim 6, wherein the distal end of each finger comprises a hook.

8. The method of claim 6, wherein each finger further comprises a sheath fixably attached at one end to the handle, wherein each sheath houses at least a portion of a respective finger.

9. The method of claim 8, wherein each distal end of the finger includes a hook-shaped member.

10. The method of claim 9, wherein each finger is individually moveable from a first position where the corresponding hook-shaped member is adjacent to a distal end of the respective sheath to a second position where the corresponding hook-shaped member is spaced away from the distal end of the respective sheath.

11. The method of claim 8, wherein each finger comprises a wire.

12. The method of claim 8, further comprising a plurality of actuator buttons, wherein each actuator button is in communication with a respective finger, and wherein each actuator button is individually operable to communicate longitudinal motion to an individual respective finger, wherein the act of individually engaging portions of the outer circumference of the anastomotic ring device with the distal ends of the elongate fingers comprises actuating the plurality of actuator buttons.

13. The method of claim 12, wherein the actuator buttons are located on the handle.

14. The method of claim 12, wherein each actuator button integrally attached to the handle further comprises a spring, wherein each of the springs is configured to bias the respective finger to a first position.

15. The method of claim 6, further comprising a sleeve actuator in communication with the sleeve, wherein the sleeve actuator is operable to communicate sliding motion to the sleeve, wherein the act of advancing the hollow sleeve comprises actuating the sleeve actuator, wherein the act of further advancing the hollow sleeve comprises further actuating the sleeve actuator.

16. The method of claim 6, wherein at least a portion of each distal ends of each finger is flared outwardly from a longitudinal axis of the sleeve.

17. The method of claim 16, wherein said distal ends of the fingers are configured to engage the anastomotic ring at separations of 120 degrees.

* * * * *